(12) United States Patent
Timmis et al.

(10) Patent No.: US 12,268,856 B2
(45) Date of Patent: Apr. 8, 2025

(54) CAP

(71) Applicant: Sanofi, Paris (FR)

(72) Inventors: William Timmis, Cambridgeshire (GB); Thomas Mark Kemp, Cambridgeshire (GB); Uwe Dasbach, Frankfurt am Main (DE)

(73) Assignee: Sanofi, Paris (FR)

( * ) Notice: Subject to any disclaimer, the term of this patent is extended or adjusted under 35 U.S.C. 154(b) by 991 days.

(21) Appl. No.: 17/281,309

(22) PCT Filed: Sep. 27, 2019

(86) PCT No.: PCT/EP2019/076170
§ 371 (c)(1),
(2) Date: Mar. 30, 2021

(87) PCT Pub. No.: WO2020/069994
PCT Pub. Date: Apr. 9, 2020

(65) Prior Publication Data
US 2021/0402102 A1  Dec. 30, 2021

(30) Foreign Application Priority Data
Oct. 1, 2018  (EP) .................................... 18306289

(51) Int. Cl.
*A61M 5/32* (2006.01)
*A61M 5/31* (2006.01)
(Continued)

(52) U.S. Cl.
CPC ........ *A61M 5/3202* (2013.01); *A61M 5/3146* (2013.01); *A61M 5/31566* (2013.01);
(Continued)

(58) Field of Classification Search
CPC .... A61M 5/3202; A61M 5/3146; A61M 5/50; A61M 5/31571; A61M 5/31566; A61M 5/3204
See application file for complete search history.

(56) References Cited

U.S. PATENT DOCUMENTS

| 2005/0165353 A1 | 7/2005 | Pessin |
| 2015/0174325 A1 | 6/2015 | Young et al. |

(Continued)

FOREIGN PATENT DOCUMENTS

| CN | 107735125 | 2/2022 |
| EP | 2745866 | 6/2014 |

(Continued)

OTHER PUBLICATIONS

PCT International Search Report and Written Opinion in International Appln No. PCT/EP2019/076170, dated Dec. 4, 2019, 9 pages.

(Continued)

*Primary Examiner* — Tasnim Mehjabin Ahmed
(74) *Attorney, Agent, or Firm* — Fish & Richardson P.C.

(57) ABSTRACT

The present disclosure relates to a cap assembly for a medicament delivery device comprising a cap body configured to be detachably mounted to a housing of a medicament delivery device, and a cap lid configured to be attached to the cap body, wherein the cap body is configured to receive a needle sleeve and the cap lid when the cap assembly is attached to a medicament delivery device, the cap lid comprising an anti-recapping element configured to prevent the cap assembly from being reattached to a housing of a medicament delivery device once the cap assembly has been removed and the medicament delivery device has been used, wherein the anti-recapping element comprises a projection configured to engage a needle sleeve of a medicament delivery device to prevent the cap assembly being reattached (Continued)

to a housing of a medicament delivery device once the medicament delivery device has been used.

20 Claims, 6 Drawing Sheets

(51) Int. Cl.
    *A61M 5/315*     (2006.01)
    *A61M 5/50*     (2006.01)

(52) U.S. Cl.
    CPC ...... *A61M 5/31571* (2013.01); *A61M 5/3204* (2013.01); *A61M 5/50* (2013.01)

(56) References Cited

U.S. PATENT DOCUMENTS

| | | |
|---|---|---|
| 2016/0325044 A1 | 11/2016 | Tschirren et al. |
| 2018/0036492 A1 | 2/2018 | Schader et al. |
| 2018/0318526 A1 | 11/2018 | Yang et al. |
| 2020/0054839 A1 | 2/2020 | Halm |
| 2020/0061309 A1* | 2/2020 | Alexandersson ... A61M 5/3204 |

FOREIGN PATENT DOCUMENTS

| | | |
|---|---|---|
| EP | 3320932 | 5/2018 |
| JP | 2005-520602 A | 7/2005 |
| JP | 2014-502888 | 2/2014 |
| JP | 2017-504425 | 2/2017 |
| WO | WO 2012/085033 | 6/2012 |
| WO | WO 2014/009705 | 1/2014 |
| WO | WO 2016/207040 | 12/2016 |
| WO | WO 2018/018164 A1 | 2/2018 |

OTHER PUBLICATIONS

PCT International Preliminary Report on Patentability in International Appln No. PCT/EP2019/076170, dated Mar. 23, 2021, 7 pages.

* cited by examiner

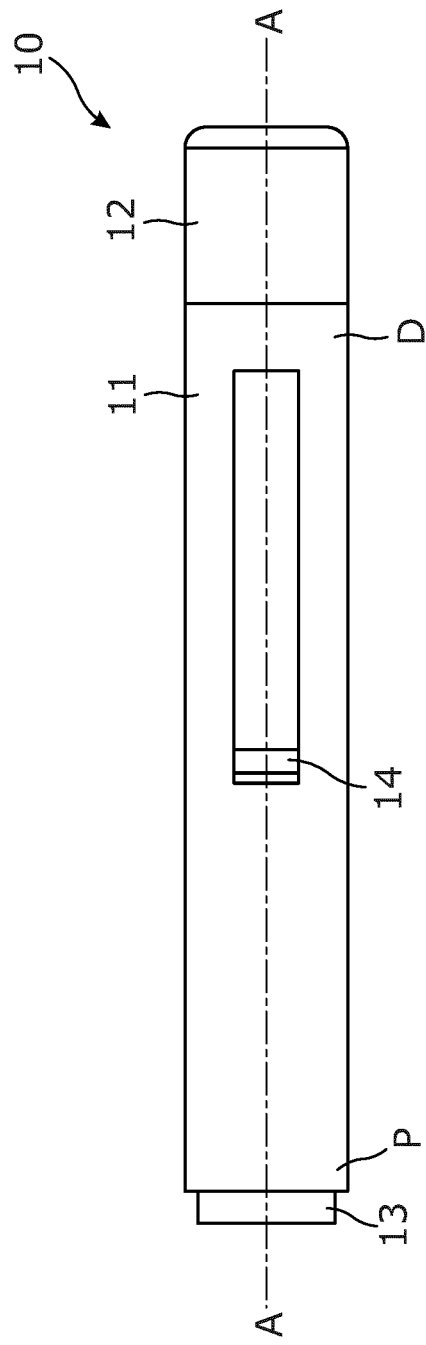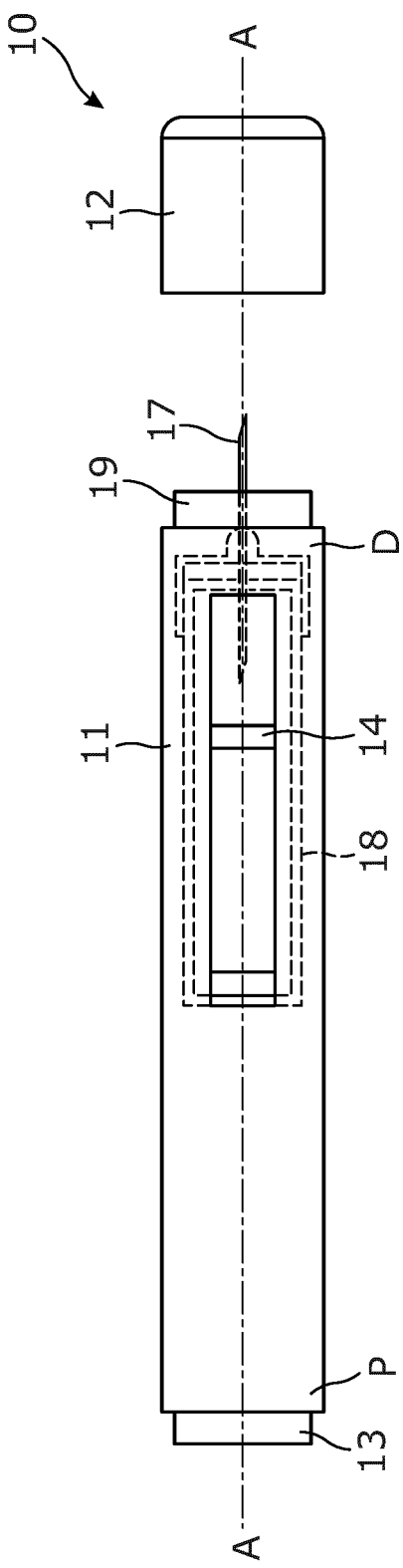

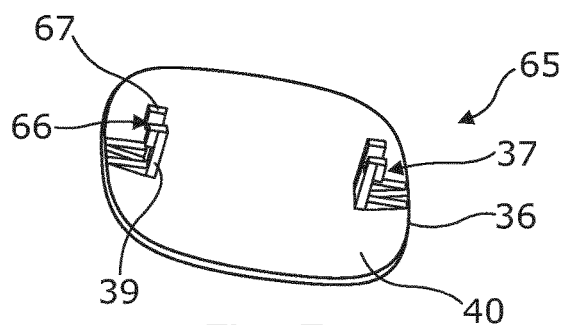
Fig. 7
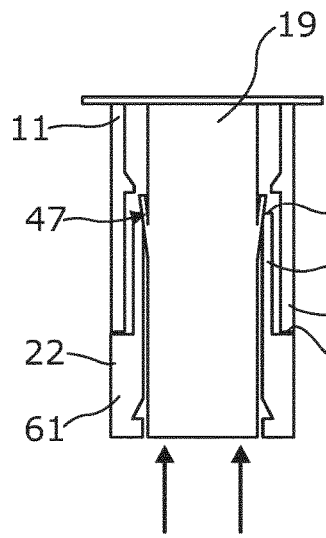
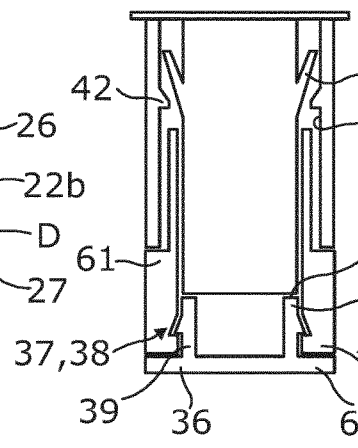
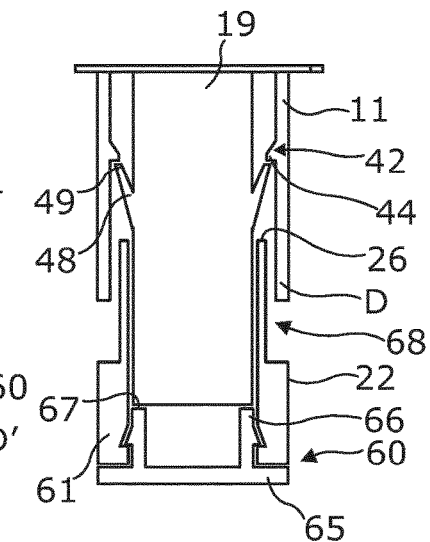
Fig. 8a  Fig. 8b  Fig. 8c
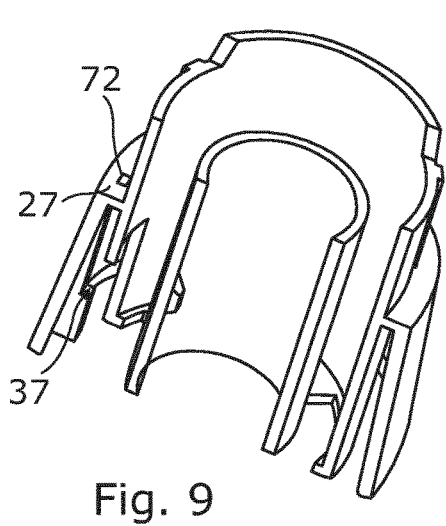
Fig. 9
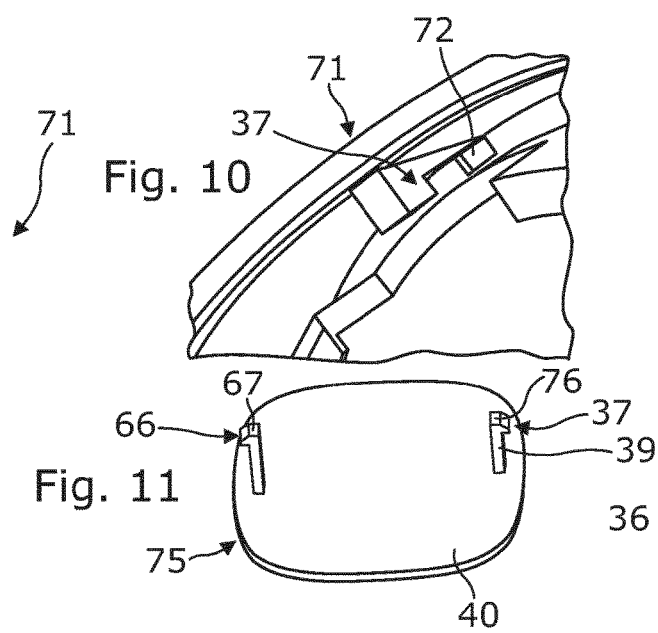
Fig. 10
Fig. 11

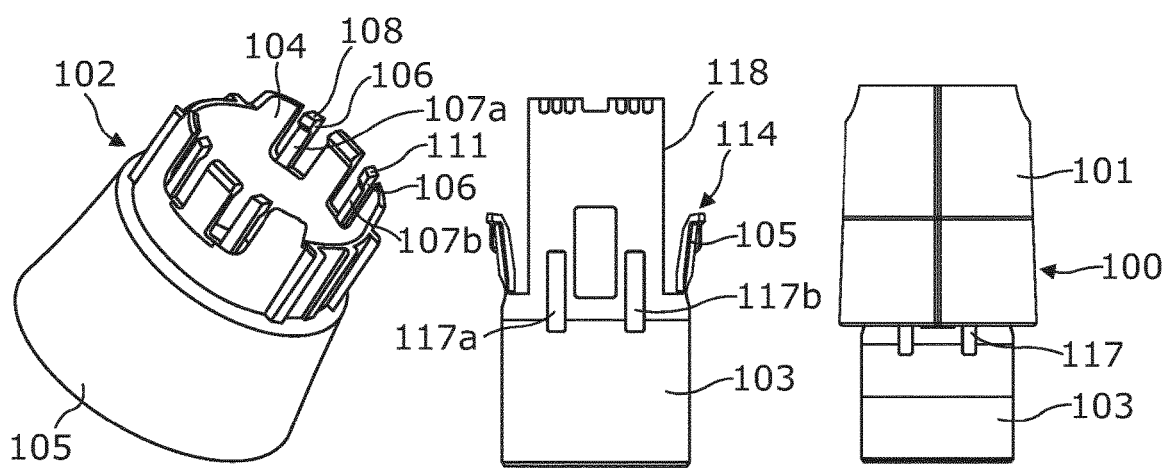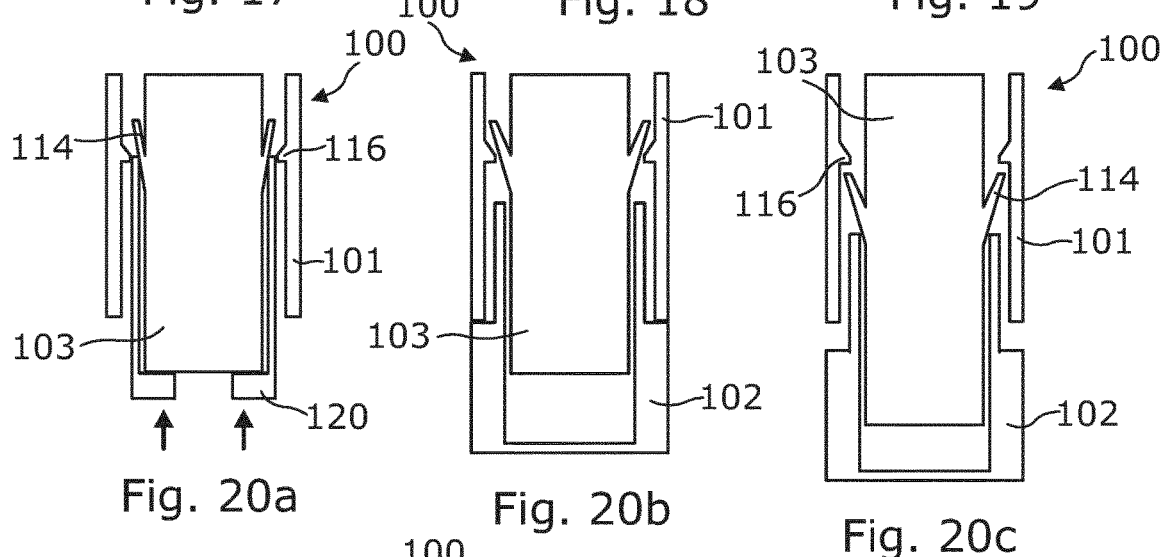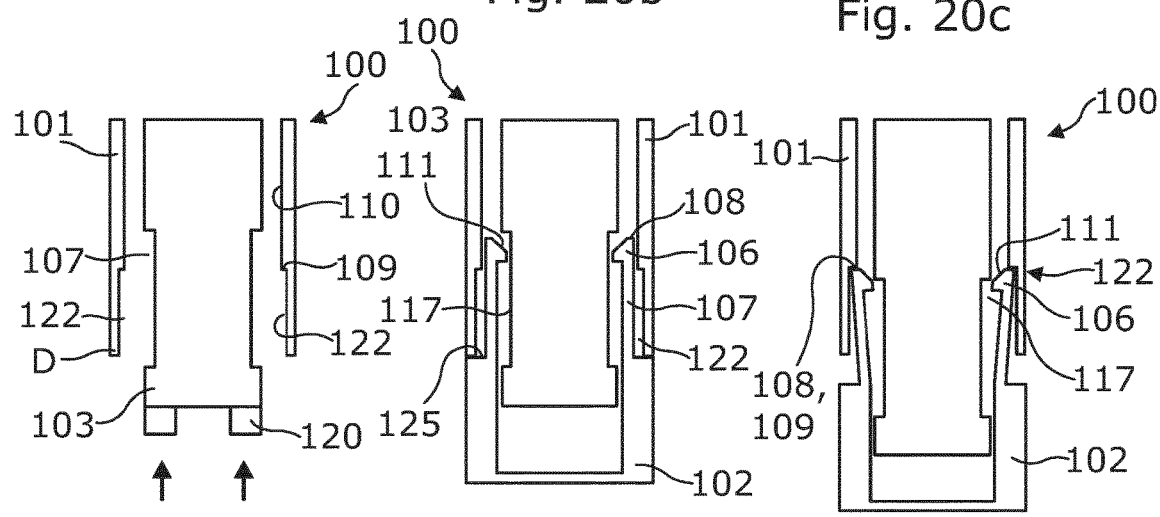

CAP

CROSS REFERENCE TO RELATED APPLICATIONS

The present application is the national stage entry of International Patent Application No. PCT/EP2019/076170, filed on Sep. 27, 2019, and claims priority to Application No. EP18306289.2, filed on Oct. 1, 2018, the disclosures of which are incorporated herein by reference.

TECHNICAL FIELD

The present disclosure relates to a cap for a medicament delivery device. The cap is particularly, but not exclusively, for an injection device. The present disclosure also relates to a method of assembling said cap and of preventing reattachment of said cap to a medicament delivery device.

BACKGROUND

Injection devices, such as auto-injectors, are known in the art for dispensing a medicament to the injection site of a patient. Such injection devices typically comprise a body and a cap. A needle syringe is located in the body and is sometimes covered by a needle guard. The cap and needle shield are removably attached to the body to shield the needle of the needle syringe. To dispense medicament, the cap and needle shield are first removed from the body to expose the needle. The needle is then inserted into the body of the patient at the injection site to dispense the medicament.

After the medicament has been delivered to the body of the patient at the injection site, the cap is then reattached to the body of a conventional injection device. However, it is then impossible to tell whether the injection device has been previously used from the cap position. Therefore, reuse of the used injection device will result in no medicament being delivered to the body of a patient and possible spread of infections and the like.

SUMMARY

According to one aspect, there is provided a cap assembly for a medicament delivery device comprising a cap body configured to be detachably mounted to a housing of a medicament delivery device, and a cap lid configured to be attached to the cap body, wherein the cap body and the cap lid are two separate components configured to be located in their ready-to-use positions on a distal end of a medicament delivery device separately, wherein the cap body is configured to receive a needle sleeve of a medicament delivery device through a proximal end of the cap body and the cap lid at a distal end of the cap body when the cap assembly is attached to a medicament delivery device in its ready-to-use position, the cap lid comprising an anti-recapping element configured to prevent the cap assembly from being reattached to a housing of a medicament delivery device once the cap assembly has been removed and the medicament delivery device has been used, wherein the anti-recapping element comprises a projection extending in the proximal direction and is configured to engage a needle sleeve of a medicament delivery device to prevent the cap assembly being fully reattached to a housing of a medicament delivery device upon attempted recapping once the medicament delivery device has been used.

The cap lid may comprise a first locking element and the cap body may comprise a second locking element, the first and second locking elements being configured to cooperate to retain the cap lid within the cap body once the cap lid is mounted on the cap body.

The projection may form the anti-recapping element extends from a lid portion of the cap lid. The first locking element may also be located on the projection.

The anti-recapping element may be configured to engage a needle sleeve when the cap lid is mounted onto the cap body in order to move a needle sleeve proximally into a ready-to-use position in a medicament delivery device.

The anti-recapping element may extend longitudinally a predetermined distance from the lid portion of the cap lid and is configured to move a needle sleeve proximally such that a second locking element on a needle sleeve is moved proximally beyond a first locking element on a main body of a medicament delivery device.

The cap body may comprise a cap lid retaining element which is configured to partially retain the cap lid within the cap body prior to mounting of the cap lid in the cap body by cooperation of the first and second locking elements of the cap lid and cap body.

The cap body may be configured to be received at least partially within a housing of a medicament delivery device.

The cap body may comprise a shoulder formed between a distal section and a proximal section of the cap body, the shoulder being configured to abut a distal end of a main body of a medicament delivery device when in a ready-to-use position.

The proximal section of the cap body may be configured to extend a predetermined distance longitudinally within a main body of a medicament delivery device to move a locking element on a needle sleeve into a non-locking position when the cap body is mounted on a main body of a medicament delivery device.

According to another aspect, there is provided a sub-assembly for a medicament delivery device comprising a housing having proximal and distal ends, the housing comprising a first locking element, a cap assembly, and a needle sleeve received at least partially within the housing and configured to be moved proximally to reveal a needle during use, the needle sleeve comprising a second locking element, wherein when the sub-assembly is in a ready-to-use position, the cap body is mounted on the distal end of the housing, the second locking element of the needle sleeve is engaged with or at least partially received in the cap body such that the second locking element is moved into a non-locking position, and the cap lid is mounted on the distal end of the cap body, and wherein after the cap assembly is removed from the housing and the sub-assembly is in a post-use position, the needle sleeve is in its post-use position and the second locking element is moved into a locking position in which the second locking element is engageable against the first locking element to at least limit the distance the needle sleeve can be moved proximally relative to the housing during attempted reattachment, the anti-recapping element of the cap lid engaging the needle sleeve to prevent the cap assembly being fully mounted on the housing once the needle sleeve is in its post-use position.

According to a further aspect, there is provided a medicament delivery device comprising a housing, a syringe having a needle at one end, a needle sleeve, and a cap assembly.

The syringe may contain a medicament.

According to another aspect, there is provided a method of priming a medicament delivery device comprising: placing a cap body over a needle sleeve; moving the cap body proximally into a housing of the medicament delivery device until a proximal end of the cap body moves a locking element of a needle sleeve into its non-locking position; moving the needle sleeve proximally until the locking element of the needle sleeve is moved proximally beyond a locking element on the housing; and moving a cap lid proximally into the cap body until it is fixedly mounted on the cap body.

The step of moving the needle sleeve and cap lid proximally relative to the housing may be completed simultaneously by using the cap lid to move the needle sleeve proximally.

According to another aspect, there is provided a cap assembly for a medicament delivery device comprising a cap body configured to be detachably mounted to a housing of a medicament delivery device, and a cap lid configured to be attached to the cap body, wherein the cap body and the cap lid are two separate components configured to be located in their ready-to-use positions on a distal end of a medicament delivery device separately, wherein the cap body is configured to receive a needle sleeve of a medicament delivery device through a proximal end of the cap body and the cap lid at a distal end of the cap body, when the cap assembly is attached to a medicament delivery device in its ready-to-use position.

According to another aspect, there is provided a cap for a medicament delivery device comprising an integrally formed cap body and cap lid configured to be detachably mounted to a housing of a medicament delivery device in a ready-to-use position, and wherein the cap body is configured to receive a needle sleeve of a medicament delivery device through a proximal end of the cap body when the cap assembly is attached to a medicament delivery device in its ready-to-use position, the cap body comprising an anti-recapping element configured to prevent the cap assembly from being reattached to a housing of a medicament delivery device once the cap assembly has been removed and the medicament delivery device has been used, wherein the anti-recapping element comprises a leg extending in the proximal direction and is configured to engage a needle sleeve of a medicament delivery device to prevent the cap assembly being fully reattached to a housing of a medicament delivery device upon attempted recapping once the medicament delivery device has been used.

BRIEF DESCRIPTION OF THE DRAWINGS

Embodiments will now be described, by way of example only, with reference to the accompanying drawings, in which:

FIG. 1A is a schematic side view of an auto-injector with a cap attached to a housing of the auto-injector.

FIG. 1B is a schematic side view of the auto-injector of FIG. 1A, with the cap removed from the housing.

FIG. 7 shows a schematic perspective view of a cap lid of a first embodiment.

FIGS. 8a to 8c show schematic cross-sectional front views of a medicament delivery device comprising an anti-recapping element, the device shown in its pre-priming position, its ready-to-use position, and its post-use position.

FIG. 9 shows a schematic cross-sectional perspective view of the cap body of a second embodiment.

FIG. 10 shows an enlarged schematic view of the cap body of FIG. 9.

FIG. 11 shows a schematic perspective view of a cap lid of a second embodiment.

FIGS. 16a to 16c 12c show schematic cross-sectional side views of a medicament delivery device of FIGS. 15a to 15c in its pre-priming position, its ready-to-use position, and its post-use position.

FIG. 17 shows a schematic perspective view of a cap.

FIG. 18 shows a schematic front view of a needle sleeve.

FIG. 19 shows a schematic front view of the needle sleeve of FIG. 18 in a housing of a medicament delivery device.

FIGS. 20a to 20c 12c show schematic cross-sectional front views of a medicament delivery device comprising the cap of FIG. 17 and the needle sleeve of FIG. 18, the device shown in its pre-priming position, its ready-to-use position, and its post-use position; and FIGS. 21a to 21c 12c show schematic cross-sectional side views of a medicament delivery device shown in FIGS. 20a to 20c in its pre-priming position, its ready-to-use position, and its post-use position.

DETAILED DESCRIPTION

Figure 2:
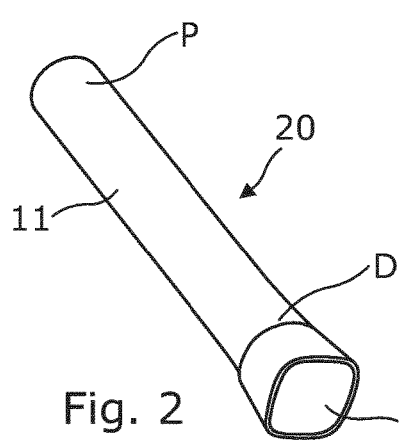
FIG. 2 shows a perspective view of a medicament delivery device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 3 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Referring now to FIG. 2, a medicament delivery device 20 is shown. As the medicament delivery device is similar to the device 10 described above, the same reference numerals will be used for the same features. As shown, the medicament delivery device 20 comprises a cap assembly 60, 70, 80 that can be detachably mounted to the housing 11. A user must remove cap 60, 70, 80 from housing 11 before device 20 can be operated.

As shown, housing 11 has a substantially square cross-section and has a substantially constant diameter along the longitudinal axis A-A. However, it will be understood that the cross-section of the housing 11 maybe any shape. The housing 11 has a distal region D and a proximal region P. The term "distal" refers to a location that is relatively closer to a site of injection, and the term "proximal" refers to a location that is relatively further away from the injection site.

Figure 3:
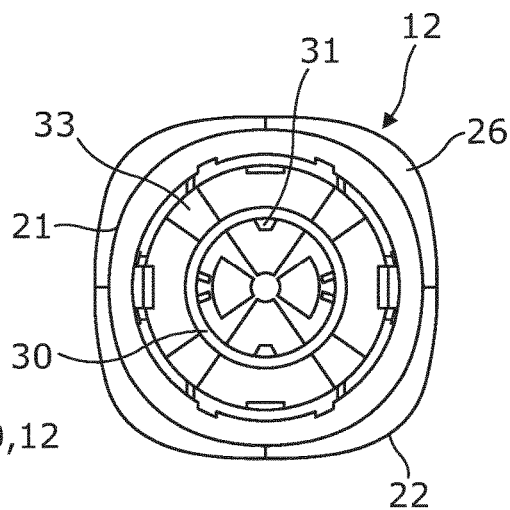
FIG. 3 shows a schematic plan view of a cap body of a first embodiment.
Figure 4:
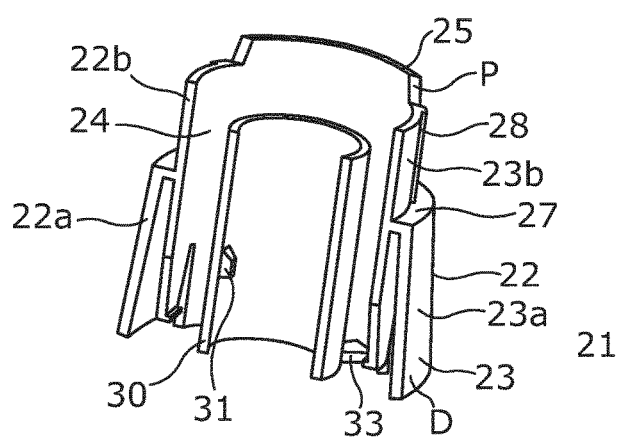
FIG. 4 shows a schematic cross-sectional perspective view of the cap body of FIG. 3.

Referring to FIGS. 3 and 4, a schematic top plan view and a perspective cross-sectional view of a part of a cap assembly 12 can be seen. It will be appreciated that the cap assembly 12 is removed from the housing 11 of the medicament delivery device 20 when a medicament in the device 20 is to be injected into a patient and so is not placed relative to a site of injection. However, in order to keep the description of the device 20 consistent, an end of the cap assembly 12 which is furthest from the housing 11 when the cap assembly 12 is mounted to the housing 11 will be referred to as the distal region D', as it is relatively closer to the end of the needle 17 when the cap assembly 12 is mounted on the housing 11. The proximal region P' of the cap assembly 12 is the region of the cap assembly 12 which is relatively further away from the tip of the needle 17 when the cap assembly 12 is mounted on the housing 11.

The part of the cap assembly 12 shown in FIGS. 3 and 4 is a cap body 21. The cap body 21 is configured to be detachably mounted on a distal end D of the housing 11 of the medicament deliver device 20. The cap assembly 12 comprises the cap body 21 and a cap lid 35, as will described in more detail hereinafter. The cap body 12 is generally tubular and comprises an open proximal end P' and a substantially open distal end D'. The open ended cap body 21 allows the cap body 21 to be tooled from both ends during manufacture and assembly, which removes the need for lifters and aids in part ejection. The proximal end P' of the cap body 21 is configured to receive a needle sleeve 19 through its open end when the cap body 21 is attached to the housing 11 in its ready-to-use position. The distal end D' of the cap body 21 is configured to receive a cap lid through its open end when a cap lid is attached to the cap body 21.

The cap body 21 comprises an outer member wall 22. The outer member wall 22 comprises an outer face 23, an inner face 24, a distal end face 25, and a proximal end face 26. The outer member wall 22 further comprises a shoulder 27 which extends around the cap body 21. The shoulder 27 is located between the distal section and the proximal section of the cap body 21. That is, the shoulder 27 is located between the distal and proximal end faces 25, 26 of the cap body 21. Preferably, the shoulder 27 is approximately in the middle of the cap body 21 in the longitudinal direction. The shoulder 27 extends substantially perpendicular to the outer member wall 22 and parallel to the end faces 25, 26. The shoulder 27 splits the outer member wall 22 into a distal section 22a and a proximal section 22b.

The proximal section 22b of the outer member wall 22 is configured to be located within the distal end of the housing 11 when the cap body 21 is mounted to the housing 11 and the device 20 is in its ready-to-use position. In its ready-to-use position, the shoulder 27 of the cap body 21 abuts the distal end of the housing 11. The proximal section 22b includes an outer face 23b of the proximal section 22b and the distal section 22a includes an outer face 23a of the distal section 23a. The cap body 21 may be held in the housing 11 by friction between the outer face 23b of the proximal section 22b of the outer member wall 22 and the inner face of the housing 11. The friction may be caused by an interference fit between the two parts. Additionally, the outer face 23b of the proximal section 22b may comprise at least one projection 28 which either causes or enhances the interference fit.

The cap body 21 may further comprise an inner member wall 30. The inner member wall 30 is tubular and generally cylindrical in shape and contained within the outer member wall 22. The inner member wall 30 may be configured to receive a needle shield (not shown). The inner member wall 30 may comprise a grabbing element 31 which is configured to grip the needle shield when the cap body 21 is mounted on the housing 11 and the device 20 is in its ready-to-use position. When the cap body 21 is subsequently removed from the housing 11, the grabbing element 31 also ensures that the needle shield 32 is also removed from the housing 11. The inner member wall 30 may be connected to the outer member wall 22 by ribs 33.

Figure 5:
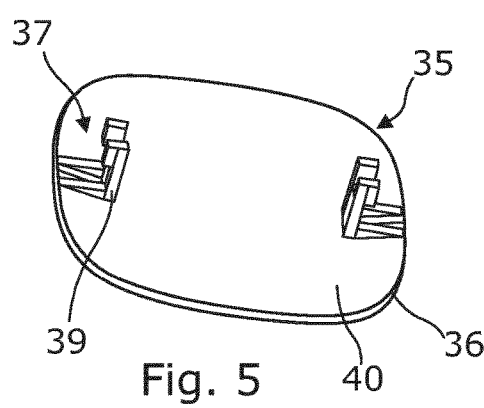
FIG. 5 shows a schematic perspective view of a cap lid.

Referring now to FIG. 5, a cap lid 35 for use with the cap assembly 12 is shown. The cap lid 35 is a separate component to the cap body 21. The cap lid 35 is connected to the rest of the medicament delivery device 20 separately to the cap body 21. The cap lid 35 is locatable within the cap body 21. The term "within" in relation to this application is intended to mean substantially within. That is, at least a portion of the cap lid 35 is configured to be received or located within the cap body 21.

The cap lid 35 comprises a lid portion 36 which is configured to close the open distal end D' of the cap body 21 when the cap lid 35 is located within the cap body 21. The cap lid 35 has a first position in which the lid portion 36 of the cap lid 35 does not close the open end D' of the cap body 21 and a second position in which the lid portion 36 of the cap lid 35 does close the open end D' of the cap body 21. The first position of the cap lid 35 shown in FIG. 5 is when the cap lid 35 is not attached to the cap body 21 and the second position is when the cap lid 35 is connected to the cap body 21.

The cap lid 35 further comprises a locking element 37. The locking element 37 is configured to fixedly attach the cap lid 35 to the cap body 21 when the cap lid 35 is mounted to the cap body 21. The cap body 21 may further comprise a corresponding locking element 38, shown in FIGS. 6a to 6c, configured to cooperate with the locking element 37 of the cap lid 35 in order to fixedly attach the cap lid 35 to the cap body 21. The locking element 38 may be located on or in the inner face 24 of the distal section 22a of the outer wall member 22. The first locking element 37 extends outwardly towards the second locking element 38 and away from the central longitudinal axis of the medicament delivery device 20.

As shown in FIG. 5, the cap lid 35 may further comprise a projection 39 extending from an inner surface 40 of the lid portion 36 of the cap lid 35. The projection 39 extends in the proximal direction. The projection may be, for example, but not limited to, a leg 39. The locking element 35 may be located on the leg 39 at a distance from the inner surface 40 of the lid portion 36 which corresponds to the distance between the distal end D' of the cap body 21 and the locking element 38 on the inner face 24 of the outer wall member 22.

The locking element 37 may be, for example, but not limited to, a snap-fitting element and the locking element 38 may be, for example, but not limited to, a snap-fitting element or a recess. As will be understood by a skilled person, there may be multiple corresponding locking elements 37, 38 on each of the cap body 21 and the cap lid 35. The locking elements 37, 38 may be glued or welded by, for example, but not limited to, ultrasonic, laser, or friction. The cooperating locking elements 37, 38 may be spaced equidistantly around the cap body 21 and cap lid 35 or may be grouped into regions. Preferably, the locking elements 37, 38 are spaced to induce an interference fit and prevent lateral movement between the cap body 21 and the cap lid 35.

Figures 6A, 6B, 6C:
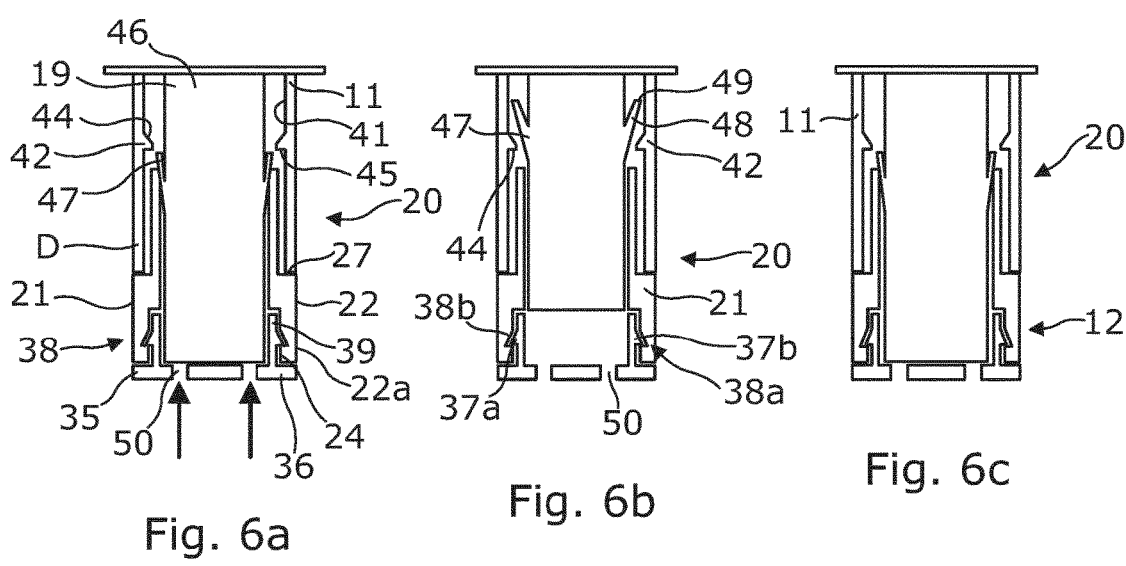
FIGS. 6a to 6c show schematic cross-sectional side views of a medicament delivery device, having the cap body of FIG. 3 and the cap lid of FIG. 5, in its pre-priming position, its ready-to-use position, and its post-use position.

Referring now to FIGS. 6a to 6c, schematic cross-sectional side views of the cap assembly 12 with the cap lid 35 shown in FIG. 5 and the housing 11 of a medicament delivery device 20 in its pre-priming position shown in FIG. 6a, in its ready-to-use position shown in FIG. 6b, and in its post-use position in FIG. 6c. The medicament delivery device 20 including the housing 11, the needle sleeve 19, and cap body 21 are part of the present embodiment, although the cap lid 35 is not.

The locking element 37 of the cap lid 35 has a generally saw-toothed profile, although it will be understood that the locking element 37 may be any other geometry that provides the locking function. The locking element 37 comprises a first surface 37a and a second surface 37b. The first surface 37a is a locking surface which is configured to prevent the cap lid 35 from being removed from the cap body 21 after it has been attached to the cap body 21.

The locking surface 37a is configured to locate in a recess 38a of the locking element 38 of the cap body 21. The recess 38a comprises a locking surface 38b which retains the locking surface 37a of the cap lid 35 within the recess 38a. The locking surfaces 37a, 38b of the locking elements 37, 38 extend generally perpendicularly to the longitudinal axis of the medicament delivery device 20. In some embodiments, the locking surfaces 37a, 38b may be inclined and extend generally in the distal direction in order to provide more reliable locking together of the two parts of the cap assembly 21.

The second surface 37b of the first locking element 37 is inclined generally in the distal direction in order to move the leg 39 inwards during attachment of the cap lid 35 to the cap body 21. The leg 39 is resiliently deformable so that once the first locking element 37 passes the second locking element 38, the leg 39 snaps back to its original position to locate the first locking element 37 in the second locking element 38 of the cap body 21.

FIG. 6a shows the distal end D of the housing 11 of the medicament delivery device 20 with a needle sleeve 19 received within the housing 11. The housing 11 is substantially hollow and comprises an inner surface 41. The inner surface 41 of the housing 11 comprises a first locking element 42. The first locking element 42 is configured to prevent, or at least limit, movement of the needle sleeve 19 in the proximal direction relative to the housing 11 beyond a predetermined point after use of the medicament delivery device 20, as will be explained in more detail hereinafter.

The first locking element 42 is also configured to allow movement of the needle sleeve 19 in the distal direction relative to the housing 11. In the present embodiment, the first locking element 42 comprises a protrusion which extends inwardly from the inner surface 41 of the housing 11. As shown in FIG. 6a, the protrusion has a generally saw-toothed profile in order to allow distal movement of the needle sleeve 19 and prevent, or at least limit, proximal movement of the needle sleeve 19 beyond a predetermined point after use of the medicament delivery device 20.

In order to achieve the above mentioned functionality, the protrusion has a first surface 44 and a second surface 45. The first surface 44 is configured to prevent the needle sleeve 19 from being moved beyond the predetermined point in the proximal direction after use of the medicament delivery device 20. The first surface 44 is an engagement surface against which the needle sleeve 19 is configured to engage to prevent, or at least limit, proximal movement of the needle sleeve 19 relative to the housing 11 beyond the predetermined point after use.

In the present embodiment of the medicament delivery device 20, the first surface 44 extends perpendicularly to the longitudinal axis of the medicament delivery device 20. That is, extends inwardly from the inner surface 41 of the housing 11 towards the central longitudinal axis of the medicament delivery device 20. However, it will be understood that the first surface 44 may be configured in any geometry in order to prevent, or at least limit, proximal movement of the needle shield 19 beyond the predetermined point. In general, the first surface 44 will face in the direction of the distal region D of the housing 11. For example, in an alternative embodiment, the first surface 44 may be inclined towards the distal region D of the housing 11.

The second surface 45 is configured to allow movement of the needle sleeve 19 beyond the predetermined point in the distal direction after use of the medicament delivery device 20 in order to allow the needle sleeve 19 to surround the entire needle 17 so that the needle 17 does not accidentally pierce the skin of a patient or care giver subsequent to the injection of medicament into the intended patient. The second surface 45 is an inclined surface against which a needle sleeve 19 is configured to engage but is able to move past without its movement in the distal direction being arrested, as will be explained in more detail hereinafter.

In the present embodiment of the medicament delivery device 20, the second surface 45 extends generally inwardly from the inner surface 41 of the housing 11 and at an inclined angle to the longitudinal axis of the medicament delivery device 20 such that it forms an acute angle. The second surface 45 is inclined such that it faces generally in the direction of the proximal region P of the housing 11. It will be understood that the second surface 45 may be configured to be any other geometry which allows movement in the distal direction of the needle sleeve 19 after the medicament has been injected into a patient. For example, the second surface 45 may comprise an arcuate profile, although alternatives are not limited to such a geometry.

The needle sleeve 19 comprises a main body 46 which is generally tubular and is configured to extend about the needle 17 when the cap assembly 12 is removed from the housing 11 of the medicament delivery device 20. During injection the needle sleeve 19 is moved in the proximal direction relative to the housing 11 to allow the needle 17 to pierce the skin of a patient.

The needle sleeve 19 further comprises a second locking element 47. The second locking element 47 is configured to cooperate with the first locking element 42 on the housing 11 to prevent, or at least limit, movement of the needle sleeve 19 in the proximal direction beyond the predetermined point after use of the medicament delivery device 20, as will be described in more detail hereinafter. The locking element 47 has a locking position in which proximal movement of the needle sleeve 19 can be prevented and a non-locking position in which proximal movement of the needle sleeve 19 may be allowed.

In the present embodiment, the second locking element 47 of the needle sleeve 19 comprises an arm 48 having a free end 49 which is located outside of the main body 46 of the needle sleeve 19 relative to the central longitudinal axis of the medicament delivery device 20.

The arm 48 of the second locking element 47 is configured to extend away from the main body 46 of the needle sleeve 19 towards the inner surface 41 of the housing 11. The arm 48 extends at an acute angle to the longitudinal axis of the medicament delivery device 20 such that it extends generally towards the proximal region P of the medicament delivery device 20. The free end 49 of the arm 48 is configured to engage the first surface 44 of the first locking element 42 of the housing 11 to prevent, or at least limit, movement of the needle sleeve 19 beyond the predetermined point. The arm 48 may be disposed or biased outwardly into its locking position and may be resiliently deformable.

In order to get to the pre-priming position shown in FIG. 6a, the needle sleeve 19 is first placed into the open distal end D of the housing 11. During initial insertion of the needle sleeve 19 into the housing 11, the locking element 47 of the needle sleeve 19 is in its locking position and so movement in the proximal direction is stopped by contact between the first surface 44 of the first locking element 42 and the free end 49 of the arm 48.

So that the free end 49 of the arm 48 of the needle sleeve 19 can be moved past the protrusion 43 of the first locking element 42, the locking element 47 must be moved into its non-locking position. To achieve this, the cap body 21 is inserted into the housing 11. The cap body 21 is inserted into the housing 11 such that the lower section 22b of the outer wall member 22 is positioned between the needle sleeve 19 and the inner surface 41 of the housing 11. The cap body 21 is configured such that the end face 26 of the outer wall member 22 can contact the arm 48 of the needle sleeve 19 when the cap body 21 is mounted to the housing 11. That is, the inner face 24 of the lower section 22b of the outer wall member 22 is substantially the same geometry and size as the needle sleeve 19.

The cap body 21 is then moved in the proximal direction until the shoulder 27 of the cap body 21 abuts the distal end D of the housing 11 of the medicament delivery device 20. As the outer wall member 22 moves in the proximal direction relative to the needle sleeve 19, the proximal end face 26 of the lower section 22b of the outer member wall 22 contacts the arm 48 of the second locking element 47. Initial contact between the proximal end face 26 of the outer member wall 22 and the arm 48 occurs proximate to the point at which the arm 48 extends from the needle sleeve 19, i.e. opposite end to the free end 49 of the arm 48.

As the cap body 21 continues to move proximally relative to the needle sleeve 19, the proximal end face 26 of the outer wall member 22 of the cap body 21 moves the arm 48 inwardly into its non-locking position. That is, the arm 48 is pivoted about the point at which it extends from the needle sleeve 19 such that the free end 49 of the arm 48 is rotated towards the needle sleeve 19 in order to substantially align the arm 48 with the longitudinal axis of the medicament delivery device 20.

When the cap body 21 is fully mounted on the housing 11, i.e. when the shoulder 27 contacts the distal end of the housing 11, the lower section 22b of the outer member wall 22 overlaps the arm 48 of the locking element 47 of the needle sleeve 19 by a distance such that the free end 49 of the arm 48 is inward of the first surface 44 of the first locking element 42 of the housing 11. Therefore, the free end 49 of the arm 48 is able to pass the first surface 44 of the locking element 42 of the housing 11 when moving in the proximal direction without contact.

Once the cap body 21 is in place, the cap lid 35 attached to the cap body 21. The cap lid 35 is pushed into the distal end of the cap body 21. As the cap lid 35 is moved proximally relative to the cap body 21 and the leg 39 moves into the cap body 21, the second surface 37b of the locking element 37 of the cap lid 35 contacts the inner face 24 of the outer member wall 22 of the cap body 21 and the leg 39 is moved inwardly towards the longitudinal axis of the medicament delivery device 20. The leg 39 moves back into its original position when the first surface 37a of the locking element 37 moves past the first surface 38b of the recess 38a of the locking element 38 on the cap body 21. When the locking elements 37, 38 cooperate the cap lid 35 is fixedly attached to the cap body 21.

The leg 39 is located on the cap lid 35 such that when the cap lid 35 is mounted to the cap body 21, the leg does not contact the needle sleeve 19. For example, as shown in FIG. 6a, the leg 39 is positioned on the lid portion 36 of the cap lid 35 so that it is aligned with the lower section 22b of the outer wall member 22 or located outward of the lower section 22b of the outer wall member 22 relative to the central longitudinal axis of the medicament delivery device 20. Thus, the leg 39 of the cap lid 35 is positioned between the upper section 22a of the outer wall member 22 and the needle sleeve 19 as shown in FIG. 6a. The cap lid 35 is pushed into the cap body 21 until the locking elements 37, 38 engage to retain the cap lid 35 within the cap body 21.

In order to move the locking element 47 of the needle sleeve 19 beyond the locking element 42 of the housing 11 in the proximally direction, a tool (not shown) is used to push the needle sleeve 19 in the proximal direction, as shown by the arrows in FIG. 6a. The tool contacts the distal end of the needle sleeve 19 through a hole 50, shown in FIG. 6a but omitted in FIG. 5, which extends through the lid portion 36 of the cap lid 35.

Referring to FIG. 6b, the tool pushes the needle sleeve 19 proximally until the free end 49 of the arm 48 moves past the first surface 44 of the first locking element 42 of the housing 11. As the needle sleeve 19 moves proximally relative to the cap body 21, the arm 48 moves out of the lower section 22b of the cap body 21 and return to its locking position.

To use the medicament delivery device 20 together with the cap assembly 12 shown in FIGS. 5 to 6c, the cap assembly 21 is removed and the device 20 used as described above. Once the device 20 has been used it is possible to mount the cap assembly 12 back onto the housing 11 as shown in FIG. 6c. The use of the cap assembly 12 using the cap lid 35 which is shown in FIGS. 5 to 6c allows re-capping of the device. However, as the cap assembly 12 can be re-mounted onto the housing 11, the position of the cap assembly 12 does not indicate to a user whether the device 20 has been used or not. The configuration of the device 20 post-use is similar to the configuration of the device before it has been primed.

Referring now to FIGS. 7 to 9c, there is shown a cap assembly 60 according to a second embodiment. The cap assembly 60 is similar to the cap assembly 12 described above with reference to FIGS. 3 to 6c with like features retaining the same reference numerals. As a result, a detailed description of the like features will be omitted herein. The cap assembly 60 comprises a cap body 61 which is the same as the cap body 21 described above.

Referring now to FIG. 7, there is shown a cap lid 65 according to another embodiment. The cap lid 65 has similar features to the cap lid 35 described above in relation to FIGS. 5 to 6c with like features retaining the same reference numerals.

There are two main differences between the cap lid 35 described above and the embodiment of the cap lid 65 shown in FIG. 7. Firstly, the cap lid 65 does not comprise holes extending though the lid portion 36 because there is no need for a tool (not shown) to prime the medicament delivery device 20 after the cap lid 65 has been mounted on the cap body 61. The removal of the holes from the cap lid 65 ensures that users are not confused about how to use the device 20, i.e. do not think that the needle 17 will extend out of a hole in the cap assembly 60 of the device 20, and the removal of holes from the exterior of the device 20 decreases the likelihood of the needle 17 becoming contaminated prior to use.

Secondly, the cap lid 65 comprises an anti-recapping element 66. The anti-recapping element 66 is configured to prevent the cap assembly 60 being fully reattached to the housing 11 of the medicament delivery device 20 once the cap assembly 60 has been removed and the medicament device 20 has been used. The anti-recapping element 66 comprises an anti-recapping surface 67 which is configured to engage the distal end D of the needle sleeve 19 when a user attempts to re-mount the cap assembly 60 on the housing 11, as will be explained in more detail hereinafter.

The anti-recapping element 66 comprises a projection 39 which extends in the proximal direction from the inner surface 40 of the lid portion 36 of the cap lid 65. That is, the anti-recapping element 66 extends from the same surface 40 of the lid portion 36 of the cap lid 65 as the locking element 37 which is located on the leg 39. In the present embodiment, both the locking element 37 and the anti-recapping surface 67 are located on the leg 39 that extends from the inner surface 40 of the lid portion 36 of the cap lid 65. Although, in an alternative embodiment, the cap lid 65 may comprise at least two legs 39, one leg 39 comprising a locking element 37 and another leg 39 forming an anti-recapping element 65, as will be seen below. Although multiple projections 39 are shown in the drawings, it will be understood that the cap lid 65 may comprise only one projection 39 or any number of projections 39.

As mentioned above, the anti-recapping surface 67 of the anti-recapping element 66 is configured such that it engages the distal end D of the needle sleeve 19 when a user attempts to re-mount the cap assembly 60. Therefore, the anti-recapping surface 67 of the anti-recapping element 66 must be located at least at the same distance from the longitudinal axis of the medicament delivery device 20 as the needle sleeve 19 or at a shorter distance so that it can contact the distal end D of the needle sleeve 19, as shown in FIGS. 8a to 8c. To achieve this, the leg 39 of the cap lid 65 may be more centrally located on the lid portion 36 of the cap lid 65 than the leg 39 of the cap lid 35.

In order to provide the anti-recapping function, the anti-recapping surface 67 of the anti-recapping element 66 formed by a projection 39 must extend into the cap body 61 such that the distance between the distal end of the needle sleeve 19 and the distal end of the arm 48 of the locking element 47 is larger than the distance between the anti-recapping surface 67 of the anti-recapping element 66 and the proximal end surface 26 of the outer wall member 22 when the cap assembly 60 is coupled, i.e. when the cap lid 65 is mounted to the cap body 61. The significance of the relative distance will now be explained with reference to FIGS. 8a to 8c.

FIG. 8a shows the first embodiment in its pre-priming position. In this position the needle sleeve 19 has been inserted into the distal end D of the housing 11 and the cap body 61 has been mounted to the distal end of the housing 11, as described above. The cap body 61 has been mounted onto the housing 11 such that the shoulder 27 of the cap body 61 abuts the distal end D of the housing 11 and the proximal end face 26 of the lower section 22b of the outer wall member 22 has moved the locking element 47 from its locking position into its non-locking position. A tool (not shown) is then used to move the needle sleeve 19 proximally, as indicated by the arrows in FIG. 8a, prior to the cap lid 65 being mounted to the cap body 61.

Once the medicament delivery device 20 has been primed as described above, the cap lid 65 is mounted to the cap body 61, as shown in FIG. 8b. The leg 39 of the cap lid 65 is placed into the open distal end D' of the cap body 61 and moved in a proximal direction until the two locking elements 37, 38 cooperate to fix the cap assembly 60 together and close the cap body 61. As illustrated, the needle sleeve 19 is moved in the proximal direction by a sufficient distance such that it needle sleeve 19 does not prevent attachment of the cap lid 65 to the cap body 61. That is, the cap lid 65 can be fully mounted to the cap body 61 without contacting the distal end of the needle sleeve 19.

The leg 39 forming the anti-recapping element 66 is configured such that the anti-recapping surface 67 is located at a distance from the proximal end face 26 of the outer wall member 22 of the cap body 61 that is greater than the distance between the distal end D of the housing 11 and the protrusion on the inner surface 41 of the housing 11.

Post-use, the housing 11 and needle sleeve 19 of the medicament delivery device 20 are in the configuration shown in FIG. 8c. The needle sleeve 19 has been moved distally relative to the housing 11 such that the free end 49 of the arms 48 of the second locking element 47 are closer to the distal end of the housing 11 than the first surface 44 of the protrusion of the first locking element 42.

When a user attempts to replace the cap assembly 60 on the housing 11, the user places the cap body 61 over the needle sleeve 19. However, during the process of moving the cap assembly 60 proximally relative to the housing 11, the anti-recapping surface 67 of the anti-recapping element 66 of the cap lid 65 engages the distal end of the needle sleeve 19.

Therefore, any further proximal movement of the cap assembly 60 would also cause proximal movement of the needle sleeve 19.

However, the anti-recapping surface 67 of the anti-recapping element 66 engages the distal end of the needle sleeve 19 before the proximal end face 26 of the cap body 61 contacts the arms 48 of the needle sleeve 19. Therefore, when the needle sleeve 19 is moved proximally, the arm 48 is in its locking position. As a result of the distance between the anti-recapping surface 67 of the anti-recapping element 66 and the proximal end face 26 of the cap body 61 being greater than the distance between the distal end D of the housing 11 and the protrusion 43 on the inner surface 41 of the housing 11, distal movement of the cap assembly 60 and the needle sleeve 19 is stopped when the free end 49 of the arm 48 engages the first surface 44 of the protrusion 43.

When the free end 49 of the arm 48 contacts the first surface 44 of the protrusion, proximal movement of the needle sleeve 19 relative to the housing 11 is prevented or at least limited. Further application of force to the cap assembly 12 by a user may result in the arm 48 deforming. However, the arm 48 will not be able to pass the protrusion and therefore, the needle sleeve 19 will not be able move substantially in the proximal direction.

Consequently, re-capping of the cap assembly 60 onto the housing 11 is prevented. Furthermore, there is a gap 68 between the shoulder 27 of the cap body 61 and the distal end D of the housing 11 which provides a visual indicator to a user that the medicament delivery device 20 has been used. Even if the arm 48 is deformed, the needle sleeve 19 will not move in the proximal direction enough for the shoulder 27 of the cap body 61 to abut the distal end D of the housing 11.

Referring now to FIGS. 9 to 12c, there is shown a cap assembly 70 according to a second embodiment. The cap assembly 70 is similar to the cap assembly 60 described above in relation to FIGS. 3, 4, 7, and 8a to 8c with like features retaining the same reference numerals. As a result, a detailed description of the like features will be omitted herein.

FIG. 9 shows a perspective cross-sectional view of a cap body 71 which is similar to the cap body 61 described with reference to the first embodiment. In the second embodiment, the cap body 71 further comprises a hole 72 extending through the shoulder 27 of the cap body 71. The hole 72 can be used for a tool (not shown) to hold the cap body during manufacture and/or assembly. Furthermore, a detailed view of the first locking element 37 of the cap body 71 can be seen. FIG. 10 provides an enlarged view of the features mentioned in relation to FIG. 9.

Referring to FIGS. 11 and 12a to 12c, a second embodiment of a cap lid 75 is shown. As in the first embodiment of the cap lid 65, the cap lid 75 of the second embodiment comprises a first locking element 37 which is located on a leg 39 which extends from an inner surface 40 of a lid portion 36. The leg 39 further comprises an anti-recapping element 66 having an anti-recapping surface 67 which is configured to prevent the re-capping of the cap assembly 70 onto the housing 11 after the medicament delivery device 20 has been used.

In FIG. 11, the first locking element 37 is shown at the end of the leg 39 opposite the lid portion 36. The proximal end of the leg 39, i.e. the end of the leg 39 opposite the lid portion 36, also comprises the anti-recapping surface 67 of the anti-recapping element 66. However, it will be understood that in an alternative embodiment, the first locking element 37 of the cap lid 75 may be located at any position along the leg 39.

In the second embodiment, the cap lid 75 further comprises a tooling surface 76. The tooling surface 76 is configured to urge the needle sleeve 19 from its pre-priming position, shown in FIG. 12a, into its ready-to-use position, shown in FIG. 12b. In this way, the cap lid 75 can be used to prime the medicament delivery device 20, as will be described in more detail hereinafter. This removes the need for two different tools to prime the device 20 and attach the cap lid 75 to the cap body 71. On the contrary, only one tool is need and both steps can be performed simultaneously. As shown in FIG. 11, the tooling surface 76 may be the same surface as the anti-recapping surface 72. However, it will be understood that the two surfaces may be distinct and separate, as shown in FIGS. 12a to 12c.

Figures 12A, 12B, 12C:
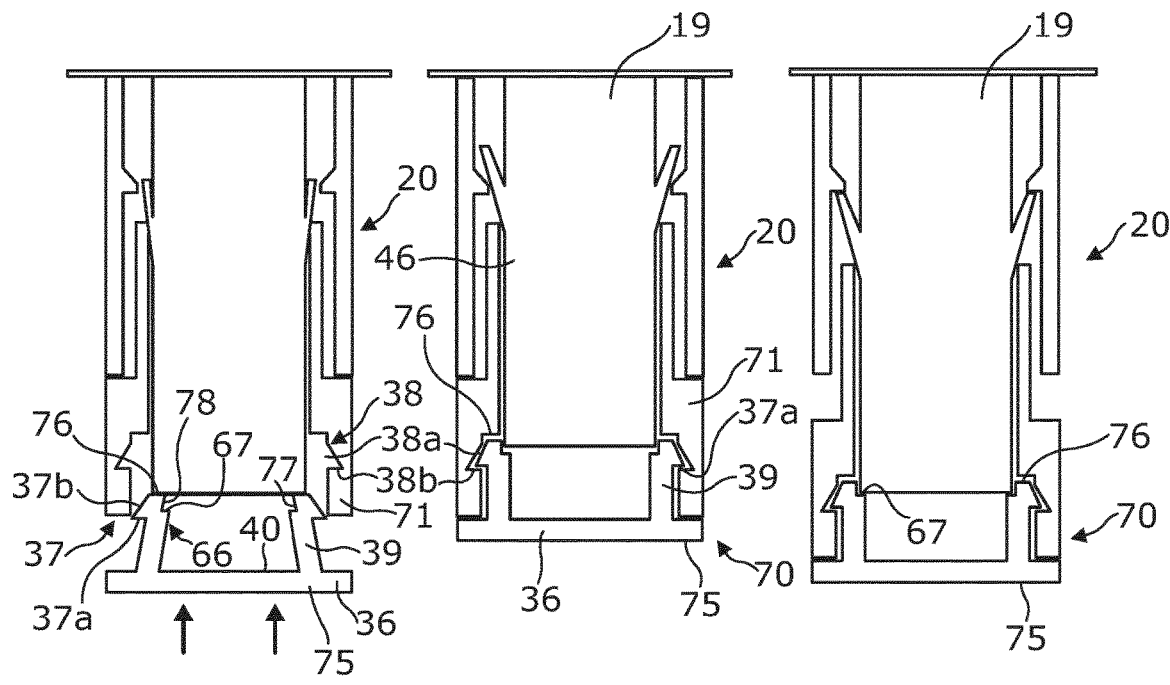
FIGS. 12a to 12c show schematic cross-sectional front views of a medicament delivery device comprising the cap lid shown in FIG. 11 and an anti-recapping element, the device shown in its pre-priming position, its ready-to-use position, and its post-use position.

Referring to FIG. 12a, the cap lid 75 comprises a leg 39 extending from the inner surface 40 of the lid portion 36. The locking element 37 is located on the proximal end of the leg 39, i.e. the end of the leg 39 opposite the lid portion 36. The locking element 37 comprises a first surface 37a and a second surface 37b, as described above in relation to the cap lid 35 shown in FIG. 5. The first surface 37a is a locking surface which is configured to engages a surface 38b of the recess 38a of the locking element 38 to prevent the cap lid 75 being removed from the cap body 71 once attached. The second surface 37b of the locking element 37 is inclined to move the leg 39 inwardly until the locking element 37 locates in the recess 38a of the locking element 38 on the cap body 21.

In FIGS. 12a to 12c the tooling surface 76 is located on the end of the leg 39. The anti-recapping surface 67 of the anti-recapping element 71 is formed parallel to but spaced from the tooling surface 76. Instead, the tooling surface 76 has a generally rectangular cut-out 77 on its inner side, closest to the longitudinal axis of the medicament delivery device 20. The cut-out 77 extends along the inner edge of the tooling surface 76. The cut-out 77 forms a first surface 78 which extends substantially parallel to the longitudinal axis of the medicament delivery device 20 and the anti-recapping surface 67 which extends substantially perpendicular to the longitudinal axis of the medicament delivery device 20.

The cut-out 77 is configured such that it extends into the tooling surface 76 by a short enough distance such that the tooling surface 76 is able to contact the needle sleeve 19 during insertion of the cap lid 75 into the cap body 71 when the leg 39 is moved inwardly but by a large enough distance that the tooling surface 76 does not contact the needle sleeve 19 during attempted recapping.

In the present embodiment, the locking element 37, the anti-recapping element 66, and the tooling surface 76 are located on the leg 39 that extends from the inner surface 40 of the lid portion 36 of the cap lid 75. Although, in an alternative embodiment, the cap lid 75 may comprise at least two legs 39, one leg 39 comprising at least one of the locking element 37, the anti-recapping surface 67, and the tooling surface 76 and another leg 39 comprising at least one of the locking element 37, the anti-recapping element 66, and the tooling surface 76. This may be achieved by varying the length and location of the legs 39 extending from the lid portion 36 of the cap lid 75.

FIG. 12a shows the medicament delivery device 20 of the present embodiment in its pre-priming position. The introduction of the cap body 71 into the housing 11 is the same as described above in relation to FIGS. 6a to 6c and 8a to 8c, therefore a detailed description will be omitted herein.

As the cap lid 75 is pushed into the open distal end D of the cap body 71, the second surface 37b of the locking element 37 at the end of the leg 39 of the cap lid 75 contacts the outer wall member 22 and is moved inwardly which bends the leg 39. The inward movement of the leg 39 causes the tooling surface 76 at the end of the leg 39 to be moved inwards and as the cap lid 75 is moved proximally relative to the cap body 71, the tooling surface 76 contacts the distal end of the needle sleeve 19.

The cap lid 75 is moved in the distal direction until the first surface 37a of the locking element 37 passes the first surface 38b of the recess 38 of the cap body 71 and the flexibly resilient leg 39 moves back to its original position to fixedly locate the cap lid 75 within the cap body 71. Simultaneously, the lid portion 36 of the cap lid 75 closes the open distal end of the needle sleeve 19. The movement of the leg 39 back into its original position relative to the lid portion 36 moves the tooling surface 76 and the first surface 78 of the cut-out 77 away from the needle sleeve 19 such that there can be no further contact between them. That is, the tooling surface 76 and the first surface 78 of the cut-out 77 are moved further away from the central longitudinal axis of the medicament delivery device 20 than the main body 46 of needle sleeve 19, as shown in FIG. 12b. Use of the medicament delivery device 20 is the same as described above and so a detailed description will be omitted herein.

FIG. 12c shows the medicament delivery device 20 of the second embodiment in its post-use configuration during attempted recapping. The recapping prevention process is the same as described above in relation to FIGS. 8a to 8c and so a detailed description will be omitted herein.

The main difference between the first embodiment and the second embodiment is that in the second embodiment, the tooling surface 76 of the cap lid 75 is moved past the needle sleeve 19 without contacting the needle sleeve 19 and the anti-recapping surface 67 contacts the needle sleeve 19 as described above to prevent recapping of the cap assembly 70 on the housing 11 of the medicament delivery device 20.

Referring now to FIGS. 13 to 16c, there is shown a cap assembly 80 according to a third embodiment. The cap assembly 80 has similar features to the cap assembly 70 described above in relation to FIGS. 9 to 12c with like features retaining the same reference numerals. As a result, a detailed description of the like features will be omitted.

Figures 13, 14:
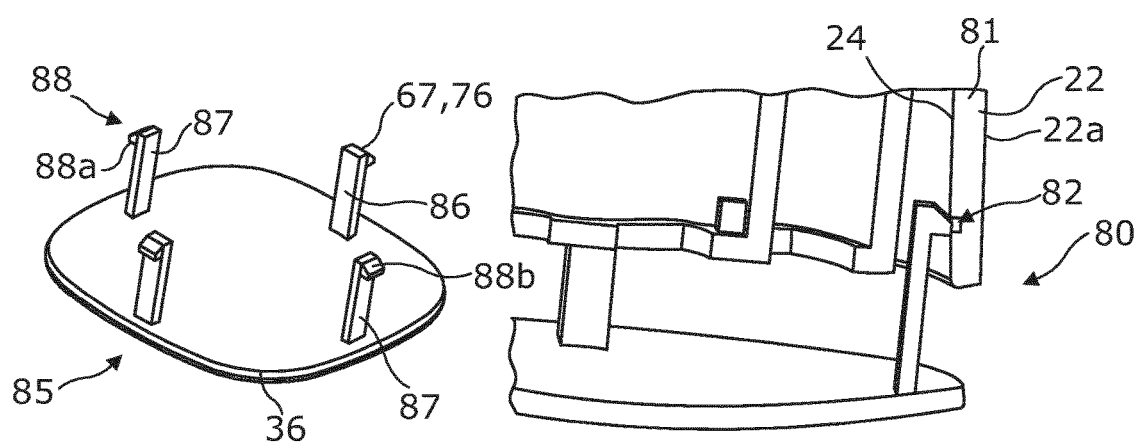
FIG. 13 shows a schematic cross-sectional perspective view of the cap lid of a third embodiment.
FIG. 14 shows a schematic cross-sectional side view of a cap body of a third embodiment partially attached to the cap lid of FIG. 13.

The cap assembly 80 of the third embodiment comprises a cap body 81, shown in FIG. 14. The cap body 81 comprises a recess 82 located near its open distal end D. In the present embodiment, the recess 82 extends for a finite distance around the inner face 24 of the distal section 22a of the outer wall member 22 of the cap body 81. The recess 82 in the inner face 24 of the cap body 81 may be longitudinally aligned with the recess 38a of the locking element 38 of the cap body 81. The recess 82 is located closer to the distal end of the cap body 81 than the recess 38a of the locking element 38.

Figures 15A, 15B, 15C:
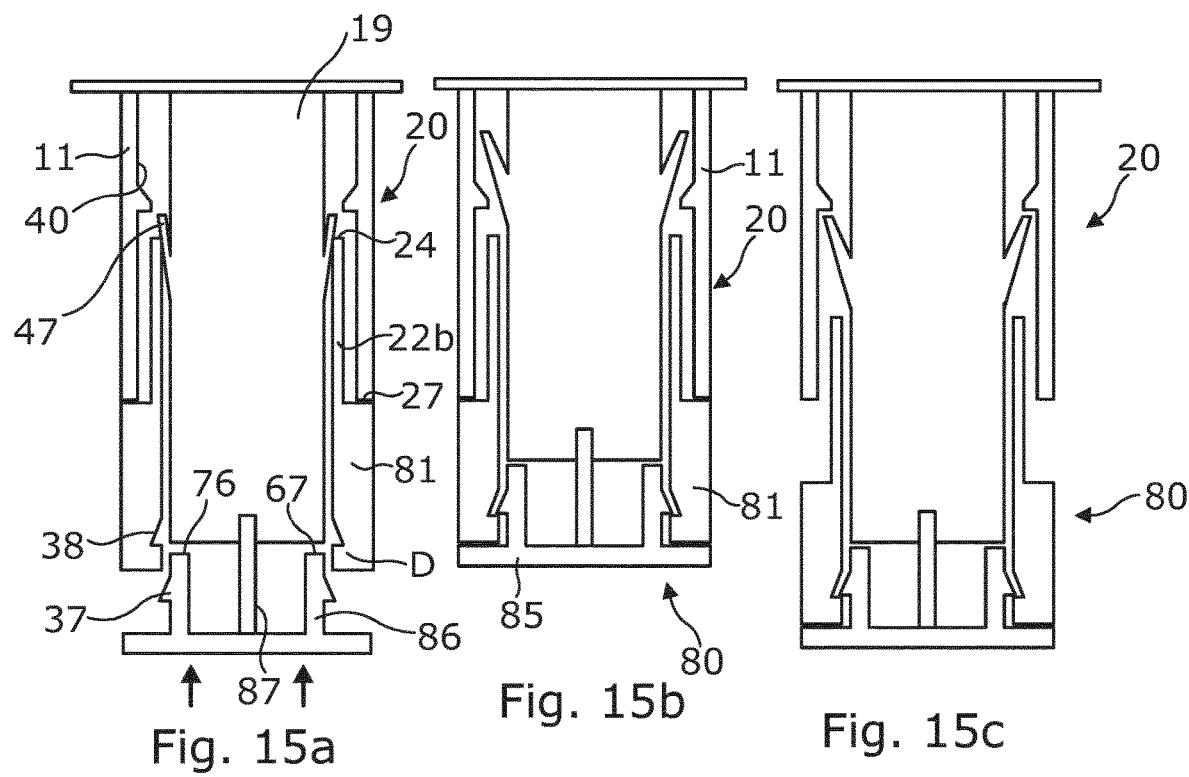
FIGS. 15a to 15c show schematic cross-sectional front views of a medicament delivery device comprising the cap lid of FIG. 13, cap body of FIG. 14, and an anti-recapping element, the device shown in its pre-priming position, its ready-to-use position, and its post-use position.

Referring back to FIG. 13, the cap lid 85 of the third embodiment comprises at least two legs 86, 87 extending from the lid portion 36 of the cap lid 85. The first leg 86, whose function is shown in FIGS. 15a to 15c, is configured similarly to the leg 39 described in relation to the second embodiment shown in FIGS. 12a to 12c. However, the anti-recapping surface 67 and the tooling surface 76 of the first leg 86 shown in FIGS. 15a to 15c are the same surface. As the first leg 86 is similar to the leg 39 described in the second embodiment and functions in the same way, a detailed description of the first leg 86 will be omitted herein.

The second leg 87 is configured to initially locate the cap lid 85 partially within the cap body 81 without closing the open distal end D of the cap body 81. The second leg 87 comprises a retaining element 88 which is located at the proximal end of the leg 87, i.e. the end of the leg 87 opposite the lid portion 36 of the cap lid 85. The retaining element 88 has a generally saw-toothed profile, similar to the profiles described in relation to the locking element 37. That is, the retaining element 88 comprises a first surface 88a configured to retain the retaining element 88 in the recess 82 on the cap body 81 and a second surface 88b which is inclined and configured to allow the retaining element 88 to be urged out of the recess 82 when a force in the proximal direction is applied. The recess 82 comprises a retaining surface 83 which is configured to cooperate with the first surface 88a in order to retain the cap lid 85 partially within the cap body 81 prior to the priming step. This is advantageous because it removes the need for a separate tool to hold the cap lid 85 in place relative to the cap body 81 prior to priming the medicament delivery device 20.

Figures 16A, 16B, 16C:
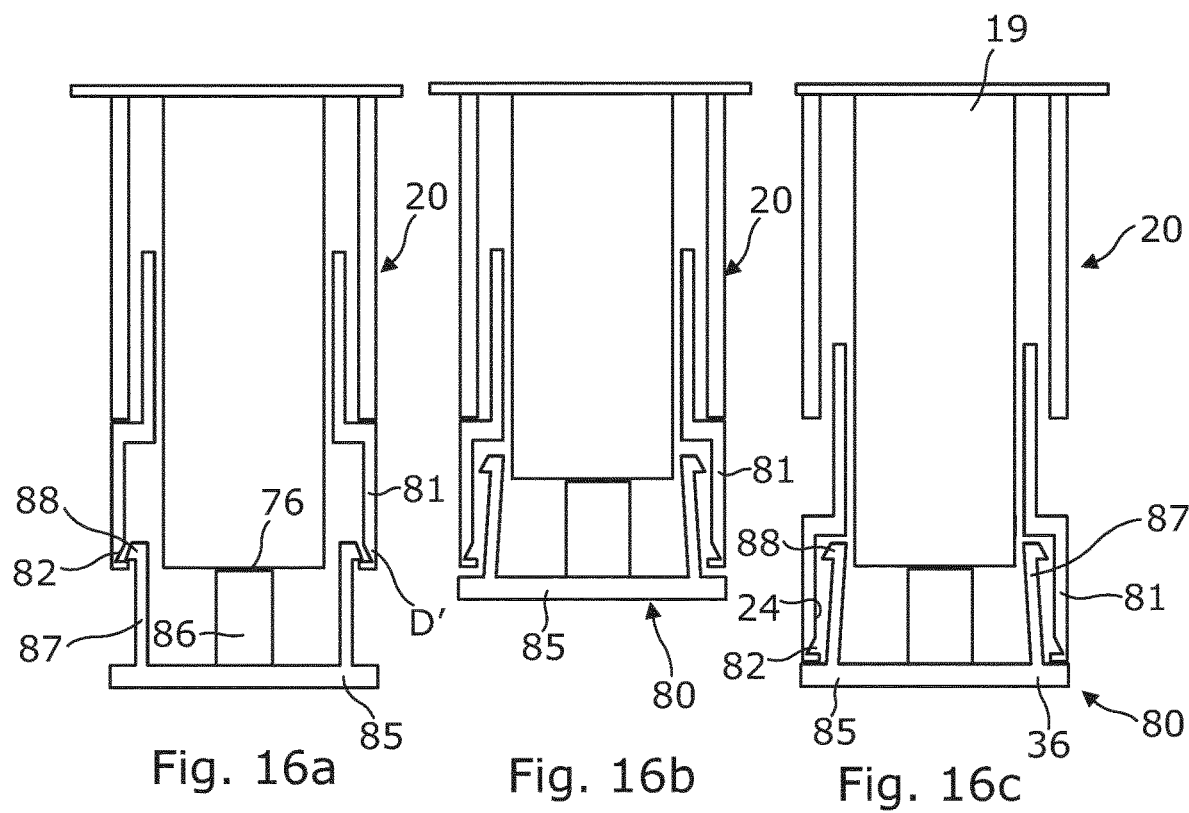

Referring now to FIG. 15a, a schematic cross-sectional front view of the third embodiment of the medicament delivery device 20, in its pre-priming position, is shown. FIG. 16a shows a schematic cross-sectional side view of the third embodiment of the medicament delivery device 20 in the same, pre-priming, position.

As with the device 20 shown in FIGS. 8a and 12a, the device 20 is placed into its pre-priming position by placing the needle sleeve 19 into the open distal end D of the housing 11 and moving the needle sleeve proximally until the locking element 37 on the needle sleeve 19 engages the locking element 38 on the inner surface 40 of the housing 11. The cap body 81 is then mounted to the housing 11 so that the lower section 22b of the outer wall member 22 is between the needle sleeve 19 and the inner surface 40 of the housing 11. As the cap body 81 is moved proximally, the proximal face 24 of the outer wall member 22 moves the locking element 47 from its locking position to its non-locking position. The cap body 81 is moved proximally until the shoulder 27 abuts the distal end D of the hosing 11.

The cap lid 85 can then be partially mounted onto the distal end D' of the cap body 81, as shown in FIG. 16a. That is, the second leg 87 of the cap lid 85 can be partially located within the cap body 81 so that the cap lid 85 is retained partially within the cap body 81 without closing the open distal end D' of the cap body 81. This is done by locating the retaining element 88 on the second leg 87 of the cap lid 85 in the recess 82 of the cap body 81.

When the retaining element 88 is located in the recess 82 of the cap body 81, as shown in FIG. 16a, the tooling surface 76 is located close to or in abutment with the distal end of the needle sleeve 19, as shown in FIG. 15a. In some embodiments, as shown in FIGS. 15a to 16c, the second leg 87 may be longer than the first leg 86 so that the cap lid 85 can be initially located in the cap body 85 without moving the needle sleeve 19 proximally and in some cases without touching the needle sleeve 19 at all. More specifically, the retaining element 88 of the second leg 87 is further from the lid portion 36 of the cap lid 85 than the tooling surface 76, anti-recapping surface 67, and locking element 47. In the embodiment shown in FIGS. 15a to 16c, the anti-recapping surface 67 and the tooling surface 76 are the same surface.

The priming process to move from the pre-priming position shown in FIGS. 15a and 16a to the ready-to-use position shown in FIGS. 15b and 16b is essentially the same as the process described above with reference to FIGS. 8a to 8c and FIGS. 12a to 12c and therefore a detail description will be omitted herein.

When the retaining element 88 is located in the recess 82 of the cap body 81, the cap lid 85 can be moved proximally to fully locate the cap lid 85 in its ready-to-use position, as shown in FIGS. 15b and 16b. It will be understood, that in one embodiment, the cap lid 85 may be attached to the cap body 81 prior to the cap body 81 being mounted onto the distal end D of the housing 11.

The anti-recapping process of the third embodiment of the medicament delivery device 20 shown in FIGS. 15c and 16c is essentially the same as the process described above with reference to FIGS. 8a to 8c and FIGS. 12a to 12c and therefore a detail description will be omitted herein. However, FIG. 16c shows that the placement of the second leg 87 on the lid portion 36 is configured such that the retaining element 88 can cooperate with the recess 82 in the inner face 24 without contacting the needle sleeve 19 at any point during priming or attempted recapping.

Referring now to FIGS. 17 to 21c, a medicament delivery device 100 is shown. The device 100 comprises a housing 101 similar to the housing 11 previously described, a cap assembly 102, and a needle sleeve 103. As shown in FIG. 17, the cap assembly 102 comprises an integral cap body 104 and cap lid 105. That is, the cap assembly 102 is formed as one piece instead of as two separate pieces. Otherwise, the cap assembly 102 is similar to the cap assembly 12 as described above.

The cap assembly 102 further comprises an anti-recapping element 106 which is located on a proximal end P' of a resiliently deformable leg 107 which extends from the proximal end of the cap assembly 102. The anti-recapping element 106 comprises an anti-recapping surface 108 which is configured to engage an abutment surface 109 on the inner surface 110 of the housing 101 which is shown in FIGS. 21a to 21c. The anti-recapping element 106 further comprises an inclined surface 111 which is configured to move the anti-recapping element 106 on the proximal end of the leg 107 outwardly relative to the central longitudinal axis of the device 100 when a user attempts to relocate the cap assembly 102 on the housing 101 after the device 100 has been used, as will be explained in more detail hereinafter.

As can be seen from FIG. 17, the cap assembly 102 has more than one leg 107. Specifically, the cap assembly 102 illustrated comprises two sets of two legs 107a, 107b extending from the lower portion of the outer wall member of the cap body 104 arranged opposite one another on the cap body 104. Each of the legs 107 may have an anti-recapping element 106 on its proximal end.

Referring to FIG. 18, a needle sleeve 103 is shown. The needle sleeve 103 comprises a locking element 114, which is shown in the form of an arm 115, which is configured to engage a locking element 116 on the housing 101 to limit proximal movement of the needle sleeve 103 relative to the housing 101, in the same way as described above. The needle sleeve 103 further comprises a recess 117 in its outer surface 118. The recess 117 extends parallel to the longitudinal axis of the device 100. The number of recesses 117a, 117b is equal to the number of anti-recapping elements 106 on the cap assembly 102. One recess 117 is configured to at least partially receive one anti-recapping element 106, as will be explained in more detail hereinafter.

Referring now to FIG. 19, the medicament delivery device 100 is shown with the needle sleeve 103 located in the housing 101 before the cap assembly 102 is mounted to the device 100 to show the device 100 prior to priming. As illustrated, the recess 117 is visible to enable the cap assembly 102 to be mounted to the housing 101. The recess 117 extends in the direction parallel to the longitudinal axis of the device 100 by a distance such that the distal end of the recess 117 is visible prior to priming of the device 100 and such that the proximal end of the recess 117 is closer to the distal end of the housing 101 than the abutment surface 109 of the housing 101 after the device 100 has been used to provide the anti-recapping function, as shown in FIG. 21c and as will be described in more detail hereinafter.

As shown in FIGS. 18, the locking element 116 of the needle sleeve 103 is spaced circumferentially from the recess 117 in the needle sleeve 103. In FIG. 18, the circumferential spacing between the locking element 116 and the recess 117 is approximately 90 degrees. However, it will be appreciated that the spacing may be different in an alternative device.

FIGS. 20a and 21a show the medicament delivery device 100 in its pre-priming position with the cap assembly 102 omitted. A tool 120 is used to move the needle sleeve 103 proximally relative to the housing 101. The tool 120 is placed over the needle sleeve 103 and move proximally, in the direction of the arrows, until the proximal end of the tool 120 contacts the locking element 114 of the needle sleeve 103 from its locking position into its non-locking position so that the locking element 114 of the needle sleeve 103 can be moved proximally past the locking element 116 on the housing 101 to prime the device 100. The tool 120 is then removed so that the cap assembly 102 can be mounted on the housing 101.

As shown in FIGS. 21a to 21c, the distal end D of the housing 101 comprises a recessed region 122 which extends proximally from a distal end face 123 of the housing 101. The recessed region 122 is formed by a cut-out extending into the inner surface 110 of the housing 101. The recessed region 122 has a proximal end formed by the abutment surface 109 which is configured to be contacted by the anti-recapping surface 108 of the anti-recapping element 106 in order to limit proximal movement of the needle sleeve 103 after the device 100 has been used and a user attempts to re-mount the cap assembly 102 on the housing 101.

FIGS. 20b and 21b show the cap assembly 102 mounted onto the housing 101 and the device 100 in its ready-to-use position. In order to mount the cap assembly 102 on the housing 101 the proximal end of the cap assembly 102 is inserted into the open distal end of the housing 101 between the needle sleeve 103 and the inner surface 110 of the housing 101. Whilst inserting the cap assembly 102, the inclined surface 111 contacts the distal end of the needle sleeve 103 and is moved outwards away from the central longitudinal axis of the device 100 towards the recessed region 122. Once the anti-recapping element 106 passes the distal end of the recess 117 the leg 107 returns to its original position and the anti-recapping element 106 partially locates in the recess 117 on the needle sleeve 103. The cap assembly 102 can then be moved proximally relative to the housing 101 until a shoulder 125 of the cap assembly 102 contacts the distal end of the housing 101, as shown in FIG. 21b.

Referring now to FIGS. 20c and 21c, shows the medicament delivery device 100 in its anti-recapping position after use. The reattachment of the cap assembly 102 to the housing 101 is similar to that described with reference to FIGS. 20b and 21b. However, in this position, the locking element 114 of the needle sleeve 103 engages the locking element 116 on the housing 101 to prevent, or at least limit, further proximal movement of the needle sleeve 103 relative to the housing 101.

Therefore, as the anti-recapping element 106 is moved proximally, the inclined surface 111 of the anti-recapping element 106 contacts the proximal end of the recess 117 in the needle sleeve 103. Consequently, the anti-recapping element 106 is moved outwards away from the central longitudinal axis of the device 100 towards the recessed region 122 until the anti-recapping surface 108 contacts the abutment surface 109 at the proximal end of the recessed region 122 to prevent further proximal movement of the cap assembly 102. In this position there is a gap between the shoulder 125 of the cap assembly 102 and the distal end of the housing 101 which indicates that the device 100 has already been used, as shown in FIG. 21c.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short-or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(wω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A cap assembly for a medicament delivery device, the cap assembly comprising:
    a cap body configured to be detachably mounted to a housing of the medicament delivery device; and
    a cap lid configured to be attached to the cap body;
    wherein the cap body and the cap lid are two separate components configured to be located in ready-to-use positions on a distal end of the medicament delivery device separately,
    wherein the cap body is configured to receive a needle sleeve of the medicament delivery device through a proximal end of the cap body and the cap lid at a distal end of the cap body when the cap assembly is attached to the medicament delivery device in the ready-to-use position of the cap body,
    wherein the cap lid comprises an anti-recapping element configured to prevent the cap assembly from being reattached to the housing of the medicament delivery device once the cap assembly has been removed and the medicament delivery device has been used,
    wherein the anti-recapping element comprises a projection extending in a proximal direction and is configured to contact and engage the needle sleeve of the medicament delivery device to prevent the cap assembly being fully reattached to the housing of the medicament delivery device upon attempted recapping once the medicament delivery device has been used.

2. The cap assembly according to claim 1, wherein the cap lid comprises a first locking element and the cap body comprises a second locking element, the first and second locking elements being configured to cooperate to retain the cap lid within the cap body once the cap lid is mounted on the cap body.

3. The cap assembly according to claim 2, wherein the projection forming the anti-recapping element extends from a lid portion of the cap lid.

4. The cap assembly according to claim 3, wherein the first locking element is also located on the projection.

5. The cap assembly according to claim 3, wherein the anti- recapping element has a tooling surface which is configured to engage the needle sleeve when the cap lid is mounted onto the cap body in order to move the medicament delivery device.

6. The cap assembly according to claim 5, wherein the anti- recapping element extends longitudinally a predetermined distance from the lid portion of the cap lid and is configured to move the needle sleeve proximally such that a second locking element on a needle sleeve is moved proximally beyond the first locking element on the housing of the medicament delivery device.

7. The cap assembly according to claim 5, wherein the cap body comprises a cap lid retaining element which is configured to partially retain the cap lid within the cap body prior to mounting of the cap lid in the cap body by cooperation of the first and second locking elements of the cap lid and the first and second locking elements of the cap body.

8. The cap assembly according to claim 1, wherein the cap body is configured to be received at least partially within the housing of the medicament delivery device.

9. The cap assembly according to claim 1, wherein the cap body comprises a shoulder formed between a distal section and a proximal section of the cap body, the shoulder being configured to abut a distal end of a main body of the medicament delivery device when the cap body is in the ready-to-use position.

10. The cap assembly according to claim 9, wherein the proximal section of the cap body is configured to extend a predetermined distance longitudinally within the housing of the medicament delivery device to move a locking element on the needle sleeve into a non-locking position when the cap body is mounted on the housing of the medicament delivery device.

11. A sub-assembly for a medicament delivery device, the sub-assembly comprising:
a housing having proximal and distal ends, the housing comprising a first locking element;
a cap assembly comprising:
a cap body configured to be detachably mounted to the housing of the medicament delivery device, and
a cap lid configured to be attached to the cap body, wherein the cap lid comprises an anti-recapping element configured to prevent the cap assembly from being reattached to the housing of the medicament delivery device once the cap assembly has been removed and the medicament delivery device has been used,
wherein the cap body and the cap lid are two separate components, wherein the cap body is configured to be located in a ready-to-use position of the cap body on a distal end of the medicament delivery device, and wherein the cap lid is configured to be located in a ready-to-use position of the cap lid; and
a needle sleeve received at least partially within the housing and configured to be moved proximally to reveal a needle during use, the needle sleeve comprising a second locking element,
wherein when the sub-assembly is in a ready-to-use position, the cap body is mounted on the distal end of the housing, the second locking element of the needle sleeve is engaged with or at least partially received in the cap body such that the second locking element is moved into a non-locking position, and the cap lid is mounted on the distal end of the cap body, and
wherein after the cap assembly is removed from the housing and the sub-assembly is in a post-use position, the needle sleeve is in a post-use position of the needle sleeve and the second locking element is moved into a locking position in which the second locking element is engageable against the first locking element to at least limit the distance the needle sleeve can be moved proximally relative to the housing during attempted reattachment,
the anti-recapping element of the cap lid engaging the needle sleeve to prevent the cap assembly being fully mounted on the housing once the needle sleeve is in a post-use position of the needle sleeve.

12. A medicament delivery device comprising:
a housing;
a syringe having a needle at one end;
a needle sleeve; and
a cap assembly comprising:
a cap body configured to be detachably mounted to the housing of the medicament delivery device; and
a cap lid configured to be attached to the cap body, wherein the cap lid comprises an anti-recapping element configured to contact and engage the needle sleeve to prevent the cap assembly from being reattached to the housing of the medicament delivery device once the cap assembly has been removed and the medicament delivery device has been used;
wherein the cap body and the cap lid are two separate components, wherein the cap body is configured to be located in a ready-to-use position of the cap body on a distal end of the medicament delivery device, and wherein the cap lid is configured to be in a ready to use position of the cap lid.

13. The medicament delivery device according to claim 12, wherein the syringe contains a medicament.

14. The medicament delivery device of claim 12, wherein the cap body is configured to receive a needle sleeve of the medicament delivery device through a proximal end of the cap body and the cap lid at a distal end of the cap body when the cap assembly is attached to the medicament delivery device in the ready-to-use position of the cap body.

15. The medicament delivery device of claim 12, wherein the anti-recapping element comprises a projection extending in the proximal direction and is configured to engage the needle sleeve of the medicament delivery device to prevent the cap assembly being fully reattached to the housing of the medicament delivery device upon attempted recapping once the medicament delivery device has been used.

16. The medicament delivery device of claim 15, wherein the cap lid comprises a first locking element and the cap body comprises a second locking element, the first and second locking elements being configured to cooperate to retain the cap lid within the cap body once the cap lid is mounted on the cap body.

17. The medicament delivery device of claim 16, wherein the projection forming the anti-recapping element extends from a lid portion of the cap lid.

18. The medicament delivery device of claim 16, wherein the first locking element is also located on the projection.

19. A method of priming a medicament delivery device comprising:
placing a cap body over a needle sleeve;
moving the cap body proximally into a housing of the medicament delivery device until a proximal end of the cap body moves a first locking element of the needle sleeve into a non-locking position;
moving the needle sleeve proximally until the locking element of the needle sleeve is moved proximally beyond a second locking element on the housing; and
moving a cap lid proximally into the cap body until it is fixedly mounted on the cap body.

20. The method according to claim 19, wherein moving the needle sleeve and moving the cap lid are completed simultaneously by using the cap lid to move the needle sleeve proximally.

* * * * *